(12) United States Patent
Lee

(10) Patent No.: US 11,590,313 B2
(45) Date of Patent: Feb. 28, 2023

(54) SMART RELAXATION MASK

(71) Applicant: BOSE CORPORATION, Framingham, MA (US)

(72) Inventor: Daniel Keewoong Lee, Boston, MA (US)

(73) Assignee: BOSE CORPORATION, Framingham, MA (US)

( * ) Notice: Subject to any disclaimer, the term of this patent is extended or adjusted under 35 U.S.C. 154(b) by 270 days.

(21) Appl. No.: 16/363,695

(22) Filed: Mar. 25, 2019

(65) Prior Publication Data

US 2020/0306493 A1    Oct. 1, 2020

(51) Int. Cl.
*A61M 21/02* (2006.01)
*A61B 5/053* (2021.01)
(Continued)

(52) U.S. Cl.
CPC ......... *A61M 21/02* (2013.01); *A61B 5/02416* (2013.01); *A61B 5/0533* (2013.01);
(Continued)

(58) Field of Classification Search
CPC ......... A61B 5/375; A61B 5/168; A61B 5/398; A61B 5/7405; A61B 5/6815; A61B 5/6803; A61B 5/378; A61B 5/165; A61B 5/7264; A61B 5/318; A61B 5/02416; A61B 5/0533; A61B 5/38; A61B 5/6804; A61B 5/7455; A61B 5/7246; A61B 5/742; A61M 2209/088; A61M 2230/65; A61M 2205/3306; A61M 2205/507; A61M 2230/04; A61M 2230/63; A61M 2205/3375; A61M 2021/0027; A61M 2230/14; A61M 2021/0044; A61M 2230/10; A61M 2230/60; A61M 2230/42;
(Continued)

(56) References Cited

U.S. PATENT DOCUMENTS 4,189,141 A    2/1980 Rooney
4,315,502 A *  2/1982 Gorges ................... A61B 5/486
                                                  434/236
(Continued)

FOREIGN PATENT DOCUMENTS

CA    2966774 A1   5/2016
JP    2011184625 A  9/2011

OTHER PUBLICATIONS

Szafir, et al., "Pay Attention! Designing Adaptive Agents That Monitor and Improve User Engagement", Session: Al & Machine-Learning and Translation, CHI 2012, May 5-10, 2012, Austin, Texas, USA, 10 pp. (Year: 2012).*
(Continued)

*Primary Examiner* — Christine H Matthews
*Assistant Examiner* — Joshua Daryl D Lannu
(74) *Attorney, Agent, or Firm* — Patterson + Sheridan, LLP

(57) ABSTRACT

Aspects of the present disclosure provide a smart relaxation mask configured to output a stimulus and collect biometric information while the stimulus is output to determine if the subject is paying attention to the stimulus. If the subject is not focused on the stimulus, the mask adjusts at least one of an audio, visual, or haptic output. The stimulus is adjusted in an effort to shift the subject's attention to the stimulus and away from racing thoughts.

21 Claims, 5 Drawing Sheets

(51) Int. Cl.
*A61B 5/024* (2006.01)
*A61B 5/16* (2006.01)
*A61B 5/00* (2006.01)
*G06F 3/16* (2006.01)
*A61B 5/0533* (2021.01)
*A61B 5/38* (2021.01)
*A61B 5/318* (2021.01)
*A61B 5/398* (2021.01)
*A61M 21/00* (2006.01)

(52) U.S. Cl.
CPC .............. *A61B 5/165* (2013.01); *A61B 5/318* (2021.01); *A61B 5/38* (2021.01); *A61B 5/398* (2021.01); *A61B 5/6803* (2013.01); *A61B 5/7264* (2013.01); *A61B 5/742* (2013.01); *A61B 5/7405* (2013.01); *A61B 5/7455* (2013.01); *G06F 3/165* (2013.01); *A61M 2021/0022* (2013.01); *A61M 2021/0027* (2013.01); *A61M 2021/0044* (2013.01); *A61M 2205/50* (2013.01); *A61M 2205/52* (2013.01); *A61M 2230/10* (2013.01)

(58) Field of Classification Search
CPC .......... A61M 21/02; A61M 2205/3592; A61M 2205/8206; A61M 2205/50; A61M 2021/0022; A61M 2205/332; A61M 2021/0083; A61M 2205/52; A61M 2230/005; A61M 230/63; A61F 9/04; G06F 3/165
See application file for complete search history.

(56) References Cited

U.S. PATENT DOCUMENTS

| | | | |
|---|---|---|---|
| 5,539,422 | A | 7/1996 | Heacock et al. |
| 7,147,319 | B2 | 12/2006 | Lin |
| 8,249,287 | B2 | 8/2012 | Silvestri et al. |
| 8,852,073 | B2 | 10/2014 | Genereux et al. |
| 9,707,409 | B2 | 7/2017 | Colbaugh |
| 10,057,675 | B2 | 8/2018 | Mankodi et al. |
| 11,089,954 | B2 | 8/2021 | Jackson et al. |
| 2004/0225340 | A1 | 11/2004 | Evans |
| 2009/0149721 | A1 | 6/2009 | Yang |
| 2010/0179389 | A1* | 7/2010 | Moroney, III ......... A61B 5/682 600/301 |
| 2011/0007929 | A1 | 1/2011 | Rabu et al. |
| 2011/0257713 | A1 | 10/2011 | Clegg et al. |
| 2012/0137406 | A1 | 6/2012 | Hide |
| 2013/0184516 | A1 | 7/2013 | Genereux et al. |
| 2015/0018927 | A1* | 1/2015 | Warschewske ....... A61M 21/00 607/141 |
| 2016/0005320 | A1* | 1/2016 | deCharms ............ A61B 8/0808 434/236 |
| 2016/0193442 | A1 | 7/2016 | Adamczyk et al. |
| 2017/0133002 | A1* | 5/2017 | Jung ................ G10K 11/17881 |
| 2017/0139211 | A1 | 5/2017 | Trail |
| 2017/0189639 | A1* | 7/2017 | Mastrianni ............ A61M 21/02 |
| 2018/0110960 | A1 | 4/2018 | Youngblood et al. |
| 2018/0184974 | A1 | 7/2018 | Cimenser et al. |
| 2018/0224673 | A1 | 8/2018 | Therrien |
| 2018/0235540 | A1 | 8/2018 | Kirszenblat et al. |
| 2018/0250494 | A1 | 9/2018 | Hanbury |
| 2018/0295439 | A1 | 10/2018 | Garrett |
| 2019/0053948 | A1 | 2/2019 | Schempp |
| 2019/0192077 | A1* | 6/2019 | Kaiser .................. A61B 5/0006 |
| 2020/0276053 | A1 | 9/2020 | Luo |
| 2021/0008332 | A1 | 1/2021 | Jin et al. |
| 2022/0134052 | A1 | 5/2022 | Luo |

OTHER PUBLICATIONS

Sleep Therapy Mask @ Sharper Image, viewed Oct. 29, 2018, 2 pp.
The Anxiety Relieving Sleep Lamp @ Sharper Image, viewed Oct. 29, 2018, 4 pp.
Szafir, et al., "Pay Attention! Designing Adaptive Agents That Monitor and Improve User Engagement", Session: AI & Machine-Learning and Translation, CHI 2012, May 5-10, 2012, Austin, Texas, USA, 10 pp.
Brabobzcz, et al., "Lost in Thoughts: Neural Markers of Low Altertness During Mind Wandering", NeuroImage, vol. 54, Issue 4, Feb. 14, 2011. pp. 3040-3047.
International Search Report and Written Opinion for International Application No. PCT/US2020/018610 dated May 8, 2020.
Kidmose, Preben, Senior Member, IEEE; Looney, David, Member IEE; Ungstrup, Michael, Member, IEEE; Rank, Mike Lind, Member, IEEE; Mandie, Danilo P, Fellow, IEEE, "A Study of Evoked Potentials From Ear-EEG", IEEE Transactions on Biomedical Engineering, vol. 60, No. 10, Oct. 2013, 7 pages.
Goverdovsky, Valentin; von Rosenberg, Wilhelm; Nakamura, Takashi; Looney, David; Sharp, David J.; Papavassiliou, Christos; Morrell Mary J.; Mandie, Danilo P.; "Hearables: Multimodal physiological in-ear sensinf", published online: 31 Uuly 2017; from Scientific Reports, www.nature.com/scientificreports, 10 pages.
Ilumy—The Smart Sleep Mask, product details; https://www.soundoasis.com/products/light-therapy/illumy-the-smart-pleep-mask/, 5 pages, Accessed on Jul. 10, 2019.
Kappel, Simon L., member, IEEE; Rank, Mike L., Member, IEEE; Toft, Hans Olaf; Anderson, Mikael; and Kidmose, Dreben, Senior member, IEEE, "Dry-Contact Electrode Ear-EEG", unpublished article; Citation information: DOI 10.1109/TBME.2018.2835778, IEEE Transactions on Biomedical Engineering, http://www.ieee.org/publications_standards/publications/rights/index.html for more information, 9 pages.
Muse™ 2, Meditation Made Easy, product description, https://choosemuse.com/muse2/, 7 pages, Accessed on Nov. 29, 2018.
Sleep Therapy Mask, Sharper Image, https://www.sharperimage.com/si/view/product/Sleep+ Therapy+Mask/204864?t;m_mmc=alsobought-_-204864-_-null&rrec=true, 4 pages Accessed on Oct. 29, 2018.
The Anxiety Relieving Sleep Lamp, Sharper Image, https:www.sharperimage.com/si/view/product/The+Anxiety It-Relieving+Sleep+Lamp/205962?p=plist2470005&utm_source=Google&utm_medium=CP . . . 4 pages, Accessed on Oct. 29, 2018.
Looney, David; Kidmose, Preben; Park, Cheolsoo; Ungstrup, Michael; Rank, Mike Lind; Rosenkranz, Karin; Mandie, Danilo P ., "The In-the-Ear Recording Concept", IEEE Pulse, Nov./Dec. 2012, 11 pages.

* cited by examiner

SMART RELAXATION MASK

FIELD

Aspects of the present disclosure relate to a smart relaxation mask configured to identify a racing mind state of a subject and, in response to the identified racing mind state, adjust at least one auditory, haptic, or visual output of the smart relaxation mask. The adjusted output of the smart relaxation mask helps a subject achieve a state of relaxation and fall and stay asleep.

BACKGROUND

Most people have had the experience of their attention drifting away from daily tasks. For example, after some time of reading, working, commuting, interacting with others, or trying to fall asleep, a subject may experience emergence of thoughts unrelated to the task they are trying to perform. Such experiences are called mind wandering episodes. Some subjects try meditation to help increase focus or relax the mind; however, mind wandering still occurs despite purposeful efforts to avoid them.

Difficulty in falling and staying asleep negatively affects a subject's health. Stress and anxiety contribute to mind wandering episodes. Accordingly, stress and anxiety contribute to some challenges in falling and staying asleep. A need exists for assisting a subject to relax, fall asleep, and stay asleep without adversely affecting the subject's health in other, unintended ways.

SUMMARY

All examples and features mentioned herein can be combined in any technically possible manner.

Aspects describe a smart relaxation mask configured to output a stimulus of different modalities. Based on correlation of monitored biometric parameters and an output stimulus, the smart relaxation mask determines when a subject's attention has drifted away from the output stimulus. In response, the smart relaxation mask adjusts one or more outputs in an effort to shift the subject's attention to the output of the mask. Accordingly, the relaxation mask creates a closed-loop experience by intelligently determining when to adjust an output of the relaxation mask. Further, the relaxation mask outputs any combination of auditory, haptic, and visual cues in an effort to refocus the subject's attention on the sensory stimulus output by the mask and, consequently, away from racing thoughts.

Aspects provide a relaxation mask comprising at least one biometric sensor configured to output data associated with a subject wearing the relaxation mask, a memory coupled to a processor, and instructions stored in the memory that, when executed, cause the processor to: output, via an electroacoustic transducer, a sensory stimulus, receive the output data from the at least one biometric sensor, correlate the output data and the sensory stimulus to identify a racing mind state, adjust one or more of an auditory, haptic, or visual stimulus of the relaxation mask in response to the identified racing mind state, and output the adjusted one or more auditory, haptic, or visual stimulus.

According to aspects, the at least one biometric sensor comprises two electrodes configured to collect an electroencephalogram (EEG) signal from at least one of the prefrontal or frontal cortex of the subject.

In aspects, the at least one biometric sensor comprises electrodes configured to collect an electroencephalogram (EEG) signal from at least one of the frontal cortex or the prefrontal cortex of the subject and at least one of: an electrooculography (EOG) signal, electrocardiogram (ECG) signal, galvanic skin response (GSR), or photoplethysmogram (PPG) signal from the forehead of the subject.

In aspects, the sensory stimulus comprises: one of a guided mediation track or soundscape.

In aspects, the output data comprises an electroencephalogram (EEG) signal and the correlating comprises determining low activity in the EEG signal when the sensory stimulus occupying a particular range of frequencies is output.

In aspects, the instructions further cause the processor to: continue to receive output data from the at least one biometric sensor after outputting the adjusted one or more auditory, haptic, or visual stimulus, continuously correlate the received output data and the adjusted one or more auditory, haptic, or visual stimulus to determine if the subject continues to have a racing mind state, and in response to determining the continued racing mind state, further adjusting and outputting at least one auditory, haptic, or visual stimulus.

In aspects, the instructions cause the processor to adjust one or more of the auditory, haptic, or visual stimulus of the relaxation mask by: introducing, via a light pipe, visual cues which modulate to coincide with the sensory stimulus.

In aspects, the processor is configured to adjust one or more of the auditory, haptic, or visual stimulus of the relaxation mask by: introducing, via a tactical motor, a haptic output in an effort to guide the subject to focus on the sensory stimulus.

In aspects, the processor is configured to adjust one or more of the auditory, haptic, or visual stimulus of the relaxation mask by: changing a simulated environment using any combination of auditory, haptic, or visual cues.

Aspects provide a relaxation mask comprising at least one biometric sensor configured to detect an electroencephalogram (EEG) signal from the frontal cortex of a subject wearing the relaxation mask, the biometric sensor providing output data, in-ear earpieces configured to output audio signals, a light pipe disposed around eye cavities of the relaxation mask, a memory coupled to a processor, and instructions stored in the memory that, when executed, cause the processor to: output, via in in-ear earpieces, a sensory stimulus, receive the output data from the at least one biometric sensor, correlate the output data and the sensory stimulus to identify a racing mind state, execute an artificial intelligence (AI) program that adjusts at least one output of the relaxation mask in response to the identified racing mind state, and output the at least one adjusted output.

In aspects, the at least one biometric sensor comprises a first electrode placed over at least one of the subject's frontal cortex or prefrontal cortex and a second electrode placed over the subject's auditory cortex.

In aspects, the instructions further cause the processor to provide an active noise reduction signal to the in-ear earpieces.

In aspects, the AI program is configured to adjust one or more of an auditory, haptic, or visual output to guide the subject to focus on the sensory stimulus.

In aspects, the instructions are configured to cause the processor to: continuously correlate the received output data and the adjusted output signal to determine the subject remains in the racing mind state, further adjust the at least one output based on the subject remaining in the racing mind state, and output the further adjusted at least one output. In aspects, the at least one adjusted signal comprises spoken words and the further adjusted at least one output comprises lights output via the light pipe, wherein the lights are modulated to correlate to the spoken words.

In aspects, the relaxation mask comprises a tactile motor. The at least one further adjusted output comprises a haptic output from the tactile motor.

In aspects, the relaxation mask comprises a transceiver, wherein the transceiver is configured to communicate with an external wireless device to receive the sensory stimulus to be output by the relaxation mask.

In aspects, the at least one biometric sensor is carried in or on at least one of the in-ear earpieces.

Aspects provide a relaxation mask comprising a first electrode configured to detect an electroencephalogram (EEG) signal from at least one of the frontal cortex or the prefrontal of a subject wearing the relaxation mask, a second electrode configured to detect at least one of an electrooculography (EOG) signal, electrocardiogram (ECG) signal, galvanic skin response (GSR), or photoplethysmogram (PPG) signal from the forehead of the subject, the second electrode providing output data, in-ear earpieces configured to output audio signals, a light pipe disposed around eye cavities of the relaxation mask, a tactile motor disposed over the temporal lobe of the subject, a processor, a memory coupled to the processor, and instructions stored in the memory that, when executed, cause the processor to: output, via in in-ear earpieces, a sensory stimulus, determine, based on a correlation of the EEG signal, the output data, and the sensory stimulus, the subject is in a racing mind state, adjust at least one output of the relaxation mask based on the determined racing mind state, and output the at least one adjusted output.

In aspects, the processor is configured to adjust the at least one output by one or more of: adjusting the sensory output, introducing at least one visual cue via the light pipe, or introducing at least one haptic cue via the tactile motor.

In aspects, the processor is configured to: continuously monitor both the EEG signal and the output data, correlate both the continuously monitored EEG signal and output data with the adjusted output to determine the subject remains in the racing mind state, and in response to a determining the subject remains in the racing mind state, further adjust the at least one adjusted output.

Advantages of a smart relaxation mask that creates a closed-loop experience to help subjects relax, fall, and stay asleep will be apparent from the description and the claims.

DETAILED DESCRIPTION

Figure 1:
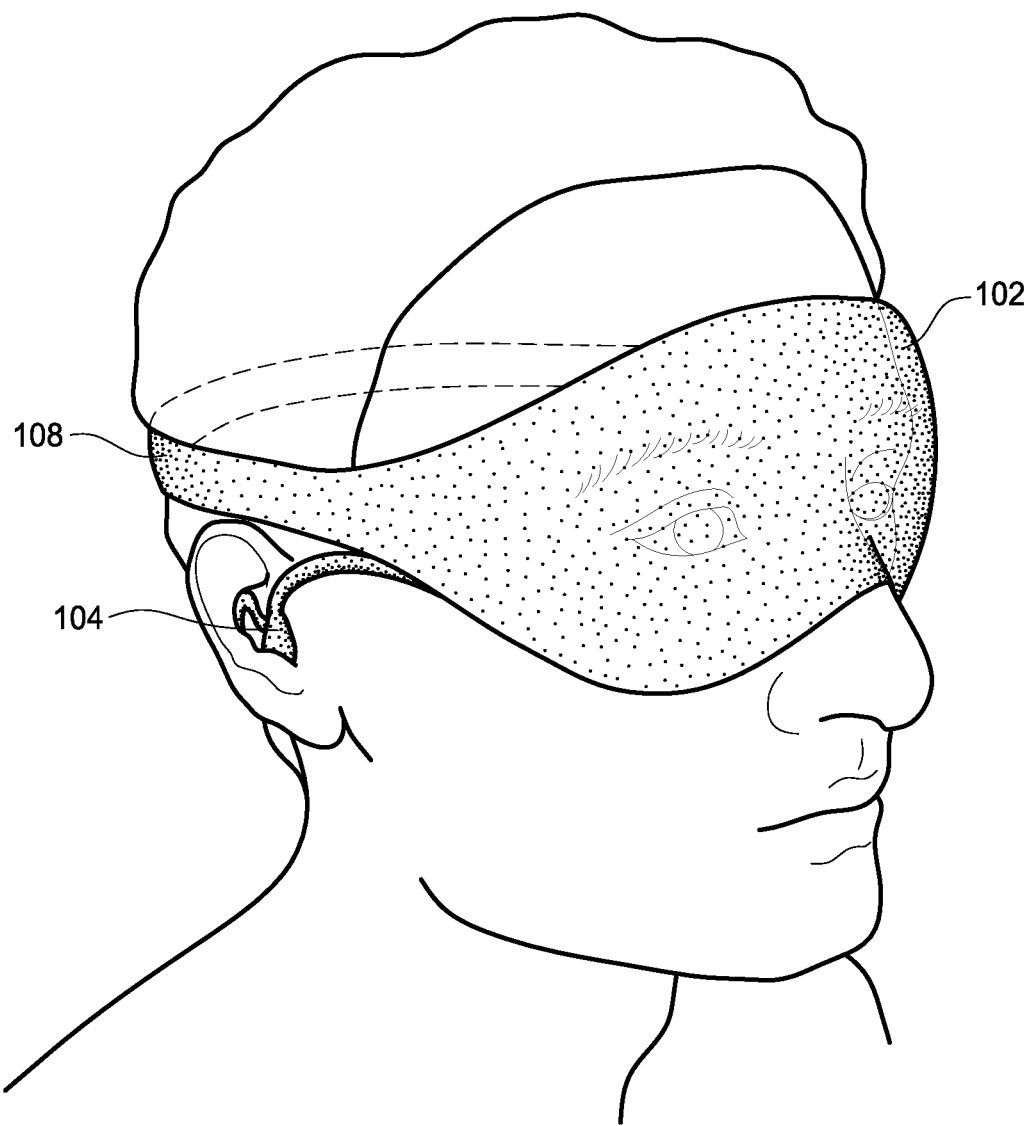
FIG. 1 illustrates an example of a smart relaxation mask on a subject.

A racing mind is characterized by racing thoughts. Racing thoughts may also be referred to as cognitive noise. Racing thoughts may focus on a single topic or several lines of thought. A subject with a racing mind ruminates over anxious thoughts, worries about something that has happened in the past, or worries about something that may happen in the future. In an example, a subject has racing thoughts about a phobia, an upcoming, potentially stressful situation, or an embarrassing moment. A racing mind may be overwhelming, increase anxiety and feelings of unease, and disrupt concentration. A subject struggles to relax, and fall and stay asleep because they have a racing mind and are ruminating on racing thoughts.

People use distraction techniques in an attempt to draw attention away from racing thoughts. Distraction techniques may help a subject focus on something that is external. Focusing on external, and perhaps more boring, thoughts help people fall asleep.

Relaxation strategies, playing music or a podcast, meditating, reading aloud, exercising, and humming are examples of distraction techniques that attempt to shift a subject's attention away from intrusive racing thoughts. Individual meditation requires some effort to focus. Guided meditation attempts to help a subject focus and guide the subject through a meditation exercise guided by a coach, written text, sound recording, video, or audiovisual media including music and/or verbal instruction.

The benefits of distraction techniques, including guided meditation, are achieved if a subject is focusing on the distraction. In an example, the distraction replaces the subject's racing thoughts, allowing the subject to relax, and eventually fall asleep. Because people are not always successful in focusing on the distraction, they may be affected by racing thoughts despite deliberate efforts and techniques to avoid them.

Aspects of the present disclosure provide a smart relaxation mask that enables closed-loop, multi-censorial cognitive noise masking. The mask includes one or more biosensors and in-ear headphones, although around-ear, on-ear, and open-air (a/k/a "open-ear") headphone configurations are also contemplated. As explained in more detail below, the mask is configured to output a multimodal sensory stimulus. The sensory stimulus may be auditory, haptic, visual, or any combination thereof. The mask monitors one or more of the subject's biometric parameters. By comparing the sensory stimulus to the subject's biometric parameters, the mask identifies if the subject is in a racing mind state. If so, the mask adjusts an output of the mask in an effort to displace racing thoughts and guide the subject to sleep.

Adjusting the output based on an identified racing mind state exposes the subject to stimulus when needed to help guide the subject to a relaxation state. Accordingly, a subject is not exposed to unnecessary stimulus from the mask, which may have negative effects on the subject.

In aspects, with the help of an artificial intelligence (AI) virtual sleep coach and a learning algorithm executed by software in communication with the mask, the mask tracks the output of mask and associated changes in biometric parameters. The mask correlates the type and content of the sensory stimulus output with identified, biophysical markers in the subject's monitored biometric parameters. In an example, the biophysical markers indicate a drop in the subject's attention. In aspects, the mask tracks which sensory output or combination of sensory outputs were successful in capturing the subject's attention. In aspects, the mask uses this historical information to output a similar content in an effort to displace racing thoughts in the future mind wandering episode and guide the subject to a state of relaxation.

FIG. 1 illustrates an example of a smart relaxation mask 102 on a subject. In FIG. 1, a front view of the mask 102 is shown on a subject. The mask 102 covers the subject's eyes and decreases or blocks the perception of light emitted from external disturbances in the subject's environment.

The mask 102 blocks or attenuates sound from the subject's environment. The mask includes integrated, in-ear headphones. In FIG. 1, a right in-ear earpiece 104 is shown. The mask includes a similar in-ear earpiece for the subject's left ear (illustrated in FIG. 2). In an example, the in-ear earpieces include a substantially frusto-conical sealing structure configured to create a gentle seal with the subject's ear canal. The headphones are configured to block or attenuate sound from the subject's environment. The headphones are also configured to output an audio stream. The audio output may include, for example, music, a voice narrative, or a soundscape. In an aspect, the in-ear headphones are configured to perform one or more of active noise reduction and active noise cancellation. The smart mask is used to assist a subject's meditation. During a break between classes, meetings, or in an effort to reduce anxiety, the active noise reduction circuity helps block noise and facilitate a meditation exercise.

As illustrated in FIG. 1, in aspects, the mask 102 wraps around the subject's head. In aspects, a strap 108 fits around the subject's head. The mask 102 has a low profile around the subject's temples.

Figure 2:
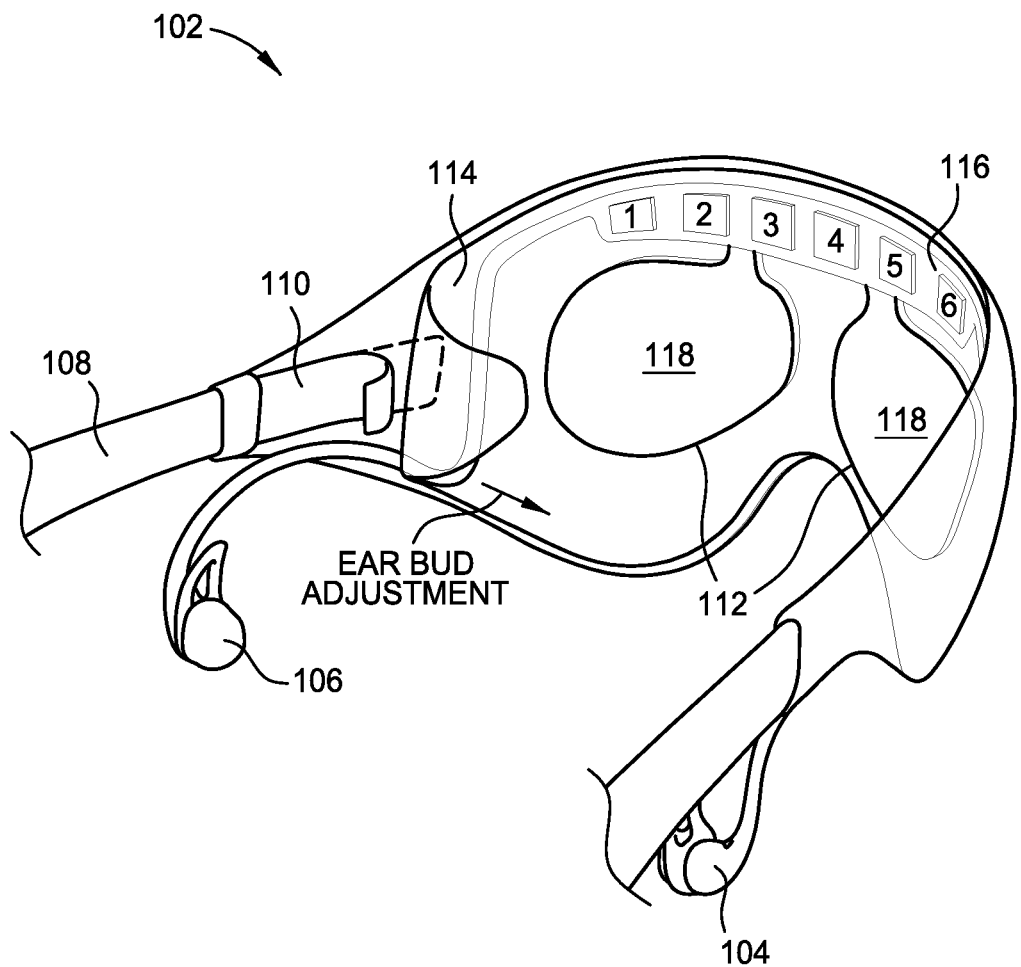
FIG. 2 illustrates an example of the backside of the smart relaxation mask, when the mask is not positioned on a subject.

FIG. 2 illustrates an example of the backside of the smart relaxation mask 102, when the mask is not positioned on a subject. As described with respect to FIG. 1, the mask 102 includes left 106 and right 104 in-ear earpieces. The mask includes a strap or band 108 that extends around a subject's head (as shown in FIG. 1). In aspects, the strap is adjustable by means of a strap adjustment mechanism 110. The strap adjustment mechanism 110 is located on one or more of the left side of the mask, as shown in FIG. 2, and the right side of the mask (not visible in FIG. 2). In an example, pulling the strap adjustment mechanism 110 away from the back of the subject's head tightens the fit of the mask 102 around the subject's head.

In aspects, the mask includes biometric electrodes or sensors. Sensors and electrodes may be used interchangeably herein. Non-limiting examples of biometric sensors include an electroencephalogram (EEG) sensor, electrooculogram (EOG) sensor, electrocardiogram (ECG) sensor, galvanic skin response (GSR) sensor, photoplethysmography (PPG) sensor, electromyogram (EMG) sensor, inertial motion (IMU) sensor, heart rate sensor, heart rate variability (HRV) sensor, respiration rate (RR) sensor, accelerometer, gyroscope, microphone, or other suitable sensor. Output from sensors are used to identify a subject's neurological markers that indicate or estimate when a subject's attention is drifting. Attention drifting may indicate the subject is in a state of rumination and is not focusing on the sensory stimulus output by the mask. The mask alters an output to displace drifting thoughts and refocus the subject's attention to the output of the mask.

As shown in FIG. 2, electrodes may be placed on one or more of contact points 1-6, the earpieces 106, or any other location on the mask. The contact points 1-6 are located above the forehead. In aspects, at least a portion of the contact points 1-6 collect signals from one or more of the frontal cortex or the prefrontal cortex. One or more electrodes, such as a subset of electrodes located on or near contact points 1-6 collect an EEG signal from the frontal cortex or prefrontal cortex and the other electrodes on or near contact points 1-6 collect signals from the forehead of a subject wearing the mask 102.

Figure 3:
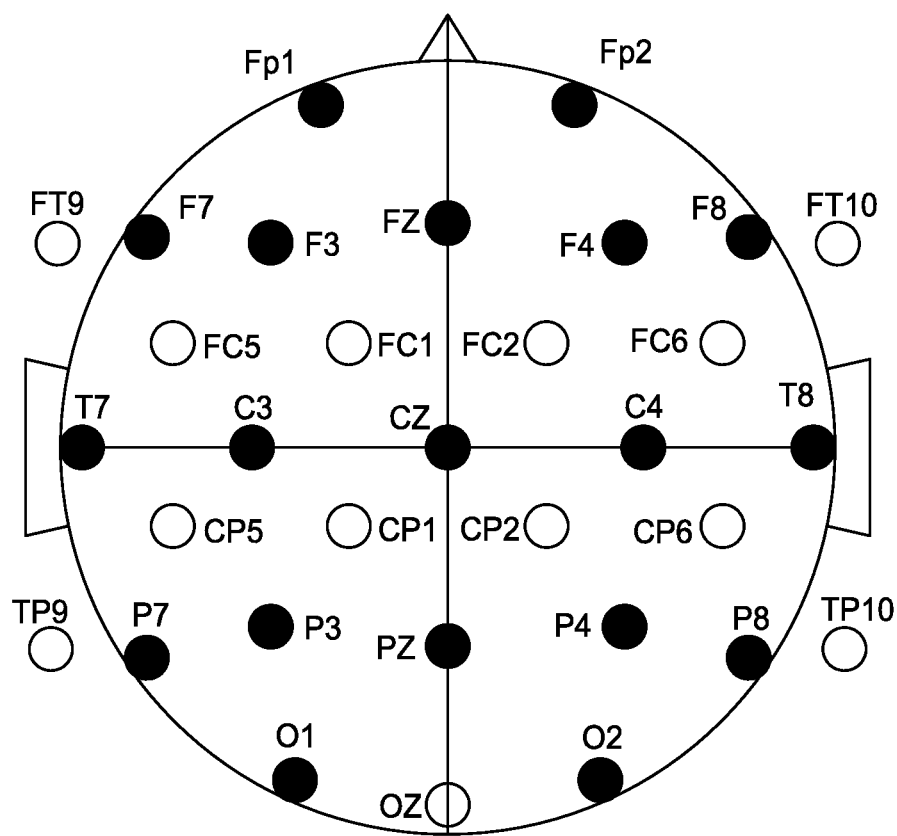
FIG. 3 illustrates an example of electrodes in the context of an EEG test according to the Modified Combinatorial Nomenclature (MCN) system.

FIG. 3 illustrates an example of sensor placement in the context of an EEG test according to the Modified Combinatorial Nomenclature (MCN) system. The MCN system is an internationally recognized system to describe the location of scalp electrodes to ensure standardized reproducibility. The electrode locations consist of letters and numbers. The letters (F, T, P, O) generally indicate the underlying lobe (frontal, temporal, parietal, and occipital) and "C" indicates the central region. Odd numbers refer to electrode placement on the left side of a head; even numbers refer to electrode placement on the right side of the head; and electrodes in the midline are annotated with "z" for zero. In addition to these, the letter codes, Fp indicates the prefrontal (or frontal pole) sites and TP indicates an area between the temporal and parietal lobes.

The form factor of the mask 102 allows placement of sensors in locations that are rich in biometric information. The collected biometric information is used to identify when a subject's attention is drifting. Drifting attention indicates the subject's focus is moving away or has moved away from the output of the mask. The subject's attention may have shifted towards anxious thoughts, making it difficult for the subject to relax, fall, and/or stay asleep.

Figure 4:
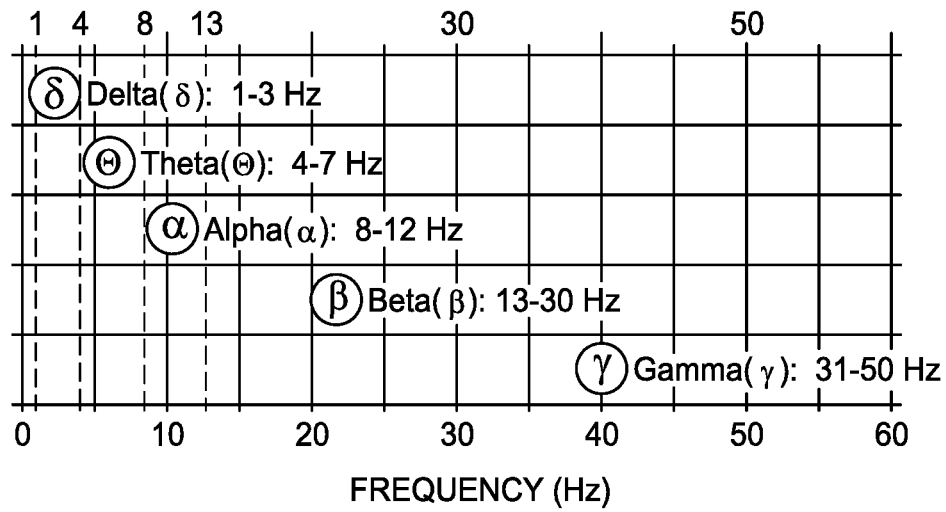
FIG. 4 illustrates example locations of alpha, theta, and beta EEG bands in an EEG and their respective frequencies.
Figure 5:
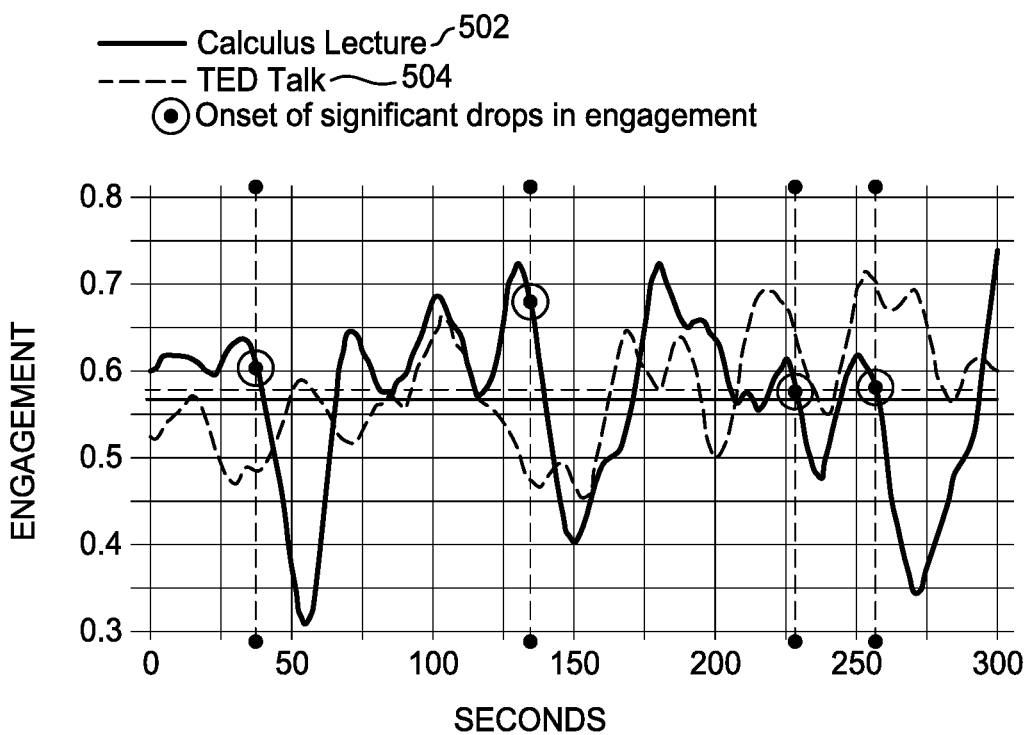
FIG. 5 illustrates example of monitored Engagement Levels of a subject involved in tasks with varying levels of engagement.

FIGS. 4 and 5 illustrate one way in which an EEG signal is used to determine a racing mind state. EEG frequencies provide insight into a subject's cognitive state including task engagement and attention. FIG. 4 illustrates example locations of alpha, theta, and beta EEG bands in an EEG and their respective frequencies. In an example, a signal E, which represents an Engagement Index, is calculated using Formula 1. Research shows that E is highly correlated with participant task engagement. See e.g., Szafir, Dan and Mutlu, Bilge. "Pay Attention! Designing Adaptive Agents that Monitor and Improve User Engagement." Session: AI & Machine-Learning & Translation. CHI 2012, May 5-10, 2012, Austin, Tex., USA.

$$E=\beta/\alpha+\theta$$  Formula 1: Engagement Index, E

FIG. 5 illustrates example monitored Engagement Levels of a subject involved in tasks with varying levels of engagement. Id. FIG. 5 shows the Engagement Index during a calculus lecture 502 and during a TED talk (video created from a presentation) 504. Dips in Engagement Indexes 502 and 504 represent attention drifting from the calculus lecture or TED talk, respectively. FIG. 5 illustrates that the Engagement Index during a calculus lecture has much more aggressive dips than the Engagement Index during a TED talk 504. FIG. 5 illustrates one example of how an EEG signal is used to determine when a subject has a racing mind; however, other methods can be used to determine a racing mind based on collected biometric information.

In aspects, a subject's Engagement Index is calculated based on an EEG signal obtained using electrodes on the mask 102. Dips in the Engagement Index indicate the subject's attention is drifting. In response to identified dips, the mask takes action to shift the subject's attention to the output of the mask and, consequently, away from racing thoughts. Determining an Engagement Index based on a subject's EEG and identifying dips in the Engagement Index is only one example of identifying a subject is in a racing mind state. Other methods are used to determine if a subject has a racing mind based on an EEG signal or other collected biometric information.

In one example, the form factor of the mask allows electrodes to be placed near the frontal cortex or prefrontal cortex, which is rich in biometric information. The frontal lobe is covered by the frontal cortex. The frontal part of the frontal cortex is covered by the prefrontal cortex. The frontal cortex performs diverse functions loosely called cognition. The prefrontal cortex manages learning, mental states, and concentration. In an example, electrodes are disposed on the mask and contact Fp1 and Fp2 (FIG. 4). In an example, any of the contact points 1-6 (FIG. 2) may contact Fp1 and Fp2. The form factor further allows electrodes to be placed near the auditory cortex. Signals collected from the auditory cortex exhibit increased electrical activity in response to a subject listening or focusing on auditory stimulus. In an example, the left 106 and right 104 in-ear earpieces include conductive ear tips that make good contact with TP9 and TP10. Accordingly, in aspects, one or more biometric sensors are disposed on the ear tips of the in-ear earpieces 104, 106. Example ear tips that may be used as part of the relaxation mask 102 are described in U.S. Patent Publication 2018/0235540, "Collecting Biologically-Relevant Information Using an Earpiece," which is incorporated by reference herein in its entirety.

In one example, the mask contacts, at least, Fp1, Fp2, TP9, and TP10. As illustrated in FIG. 2, some electrodes on the mask, such as electrodes disposed at contact points 1-6, are located at or around Fp1 and Fp2. In one example, one or more of an EEG, EOG, and ECG electrode are located at contact points 1, 3, and 6, a GSR electrode is located at contact points 2 and 5, and a PPG electrode is located at contact point 4. In one specific example, an EEG electrode is disposed on at least two of contact points 1-6. Electrodes disposed on the in-ear ear tips contact TP9 and TP10.

The electrodes or sensors may be placed anywhere on the mask for measuring auditory attention and/or relaxation staging. An example configuration of electrodes is illustrated in FIG. 2; however, aspects cover other configurations of electrodes that collect biometric information used to estimate a subject's attention. In an aspect, some electrodes are disposed on the mask and other electrodes or sensors are external to the mask. An application facilitates communication between electrodes and sensors disposed on and off the mask.

In an aspect, the mask 102 includes a pair of eye cavities 118. The eye cavities serve as light barriers that cover the subject's eyes. In an example, a light emitting diode (LED) light pipe or a light pipe diffuser 112 outputs light that the subject receives through closed eyelids. The light pipe or light pipe diffuser 112 may be disposed, at least partially around or near the eye cavities 118.

In an aspect, the light pipe or the light pipe diffuser 112 creates a gentle light-based, wake-up experience. In one example, the light pipe is associated with an alarm application executed on the mask or a paired device. At a predetermined time before the alarm is set to go off, the light pipe begins to imperceptibly glow and the intensity of the light slowly increase, mimicking a beautiful sunrise. In an example, the light pipe or light pipe diffuser 112 outputs lights to create a light-based relaxation or entrainment experience. The light-based relaxation experience or entrainment experience may be either open-loop or closed-loop based on a subject's biometric parameters. For an open-loop experience, a subject may instruct the relaxation mask, by a voice activated command or user input, to begin a light-based relaxation exercise. For a closed-loop experience, the light output is adjusted, at times in combination with other sensory stimulus, to relax the subject and entrain breathing.

In aspects, the mask includes one or more mechanisms to output a haptic stimulus. In one example, the mask includes a tactile motor configured to vibrate. The motor may be located along the strap 108, above the subject's temporal region, or anywhere else on the mask.

The mask 102 includes electronics and a battery 116. The electronics may include any combination of a memory and processor, communication unit, a transceiver, a microphone and an audio output transducer or speaker. In aspects, these electronics are disposed anywhere on the mask 102. In aspects any one of the electronics are located on a device external to and in wireless communication with the mask 102.

The processor controls the general operation of the mask 102. For example, the processor performs process and control for audio and/or data communication. The processor is configured to measure, receive, calculate, or detect at least one biometric parameter of the subject. In aspects, the processor executes an AI program that takes action to regain a subject's attention by adjusting an output of the mask. In aspects, the AI program performs functions of a personalized sleep coach.

In combination with the audio output transducer, the processor is configured to output a sensory stimulus. The processor receives the output data from at least one biometric sensor. The processor, optionally in combination with a wireless communication unit, correlates the output data and the sensory stimulus to identify a racing mind state. In response to an identified racing mind, the processor, in combination with the transducer, haptic motor, and/or light pipes/diffusers 112 adjusts and outputs one or more of an adjusted auditory, haptic, or visual stimulus. The biometric sensors are configured to continuously monitor a subject's biometric parameters in an effort to determine if the subject remains in a racing mind state. If so, the processor, in combination with the transducer, haptic motor, and/or light pipes/diffusers 112 adjusts an output of the mask to regain the subject's attention and displace wandering thoughts. As described in more detail below, the mask has the ability to output multi-modal outputs. Upon determining that the subject remains in a racing mind state, the mask varies the type of sensory output or outputs a combination of sensory outputs.

The communication unit facilitates a wireless connection with one or more other wireless devices, such as with other devices in the subject's vicinity. For example, the communication unit may include one or more wireless protocol engines such as a Bluetooth engine. While Bluetooth is used as an example protocol, other communication protocols may also be used. Some examples include Bluetooth Low Energy (BLE), NFC, IEEE 802.11, WiFi, or other local area network (LAN) or personal area network (PAN) protocols. The mask 102 may wirelessly receive audio files or processed information associated with dips in attention via the communication unit. Additionally or alternatively, the communication unit may receive information associated with a subject's biometric parameters, obtained via a contactless sensor, such as a radio frequency (RF) sensor, a radar sensor, or an under-the-bed accelerometer The transceiver transmits and receives information via one or more antennae to exchange information with one or more other wireless devices. The transceiver may be used to communicate with other devices in the subject's vicinity, such as a bedside unit, a smartphone, and/or a smartwatch. The transceiver may receive a sensory stimulus to be output by the relaxation mask from an external wireless device or a network.

The mask 102 includes an audio output transducer, which may be also known as a driver or speaker. In some examples, more than one output transducer is used. The transducer converts electrical signals into sound and converts sound into electrical signals. The transducer is configured to output an auditory stimulus to a subject. The auditory stimulus may be, for example, a guided meditation exercise, soundscape, or music. The transducer outputs audio signals, including adjusted audio signals in an effort to displace racing thoughts.

In an example, a washable liner 114 covers the strap adjustment mechanism 110, electrode contacts 1-6, electronics and battery 116, the light pipes/diffuser 112, and eye cavities 118. The washable liner 114 is removable from the mask 102.

Figure 6:
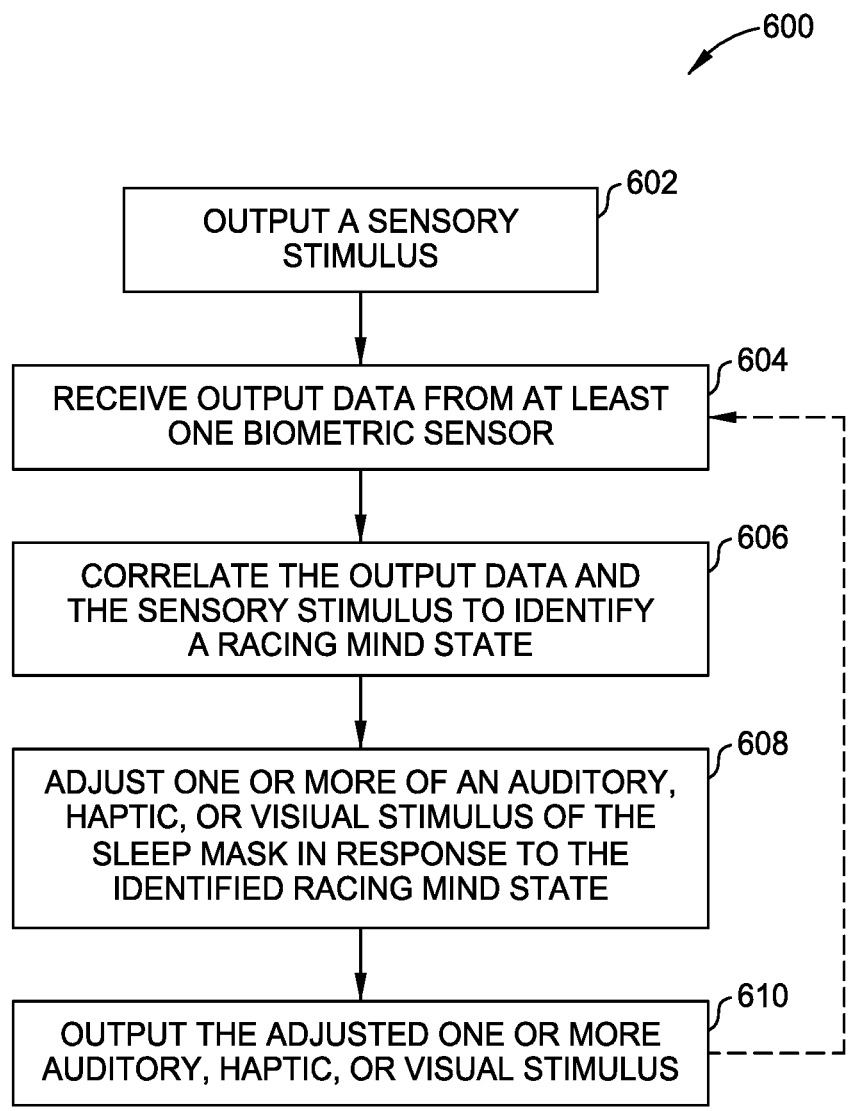
FIG. 6 illustrates example operations performed in accordance with aspects described herein.

FIG. 6 illustrates example operations 600 performed by a relaxation mask, such as the mask 102. At 602, the mask outputs, via an electroacoustic transducer, a sensory stimulus. In aspects, the sensory stimulus includes a guided meditation track, a soundscape, or music. In an example, the sensory stimulus has at least an auditory component output via in-ear earpieces.

At 604, the mask receives output data associated with a subject wearing the mask. The output data is obtained using at least one biometric sensor. The output data includes information collected using one or more biometric sensors. The biometric sensors include any combination of, for example, electrodes or sensors configured to collect or determine an EEG, EOG, ECG, GSR, or PPG. In an example, and EEG signals is collected from the frontal cortex or the prefrontal cortex. Other signals are collected from the forehead. In aspects, the EEG signal is collected from the frontal cortex or the prefrontal cortex and another signal is collected from the auditory cortex.

At 606, the mask correlates the output data and the sensory stimulus to identify if the subject has a racing mind. In aspects, a processor onboard the mask processes the output data, for example, to determine an Engagement Index and identify any dips in the Engagement Index. In aspects, the mask transmits an indication of the data to an external device or a network. Examples of external devices include a cell phone, computer, tablet, or any smart device. The external device or network processes the output data and transmits the processed data to the mask. The mask correlates the processed data with the sensory stimulus to determine if the subject is paying attention to the sensory stimulus or if the subject's attention is drifting away from the sensory stimulus. If the subject's attention is drifting away from the sensory stimulus, the mask determines the subject is in a racing mind state. In aspects, output from multiple sensors and multiple types of sensors are used in combination to determine, with increased confidence, if a subject has a racing mind.

If the subject is determined to have a racing mind, at 608, the mask adjusts one or more of an auditory, haptic, or visual stimulus. At 610, the mask outputs the adjusted one or more auditory, haptic, or visual stimulus.

In one example, the sensory stimulus output at 602 includes an auditory output. At 608, if the subject is determined to have a racing mind, the mask adjusts the stimulus by outputting lights via the light pipes/diffuser 112. In an aspect, the lights are modulated to correlate or coincide with the audio output. In an example, LED lights are flashed to match prompts by an AI program to help regain the subject's attention.

In another example, at 602, an AI program is describing an environment or setting that may be calming to the subject, such as a campfire setting. In an example, the AI program output sounds typically heard in a campfire setting, such as rustling leaves and burning wood. At 608, if the subject is determined to have a racing mind, the mask adjusts the stimulus by outputting lights via the light pipes/diffuser 112 that emulate the glow of a campfire. In an aspect, the subject is determined to have a racing mind. At 608, the mask adjusts the stimulus by introducing a haptic output such as a vibration in an effort to guide the subject to focus on the output of the AI program. In an aspect, if the subject is determined to have a racing mind, the mask changes the simulated environment, for example, from the campfire setting described above, to the sounds of waves rolling on a beach.

In aspects, as illustrated in FIG. 6, the mask continues to receive output data from at least one biometric sensor after outputting adjusted one or more auditory, haptic, or visual stimulus. The mask continuously correlates received output data from at least one biometric sensor and the adjusted one or more auditory, haptic, or visual stimulus to determine if the subject continues to have a racing mind. If so, the mask further adjusts and outputs a further adjusts at least one auditory, haptic, or visual stimulus. In aspects, when the subject is determined to be asleep, based on collected biometric information, the mask outputs masking sounds in an effort to block environment noises. In other aspects, the mask reduces sound pressure level of auditory stimulus and gradually stops outputting any visual or haptic stimuli. According to aspects, the mask eventually stops outputting a sensory stimulus and only outputs masking sounds.

The mask is configured to adjust any combination of auditory, haptic, or visual stimulus in an effort to recapture a subject's attention. The following description provides examples of output stimulus, determining the subject has a racing mind and adjusting the output stimulus based on an identified racing mind for illustrative purposes.

In an example, the sensory stimulus includes a low-frequency component that occupies, for example, frequencies in the range of approximately 20 Hz to 125 Hz. An EEG or other biometric parameters indicate if the subject is paying attention to the low-frequency component included in the sensory stimulus. Absence of activity in the EEG signal or other biometric signals indicate a subject's mind may be wandering. In response, to a wandering mind, the mask adjusts an output to regain the subject's attention.

In one example, the mask initially outputs an auditory stimulus such as a virtual sleep coach narrating a story. If one or more biometric parameters indicate the subject is in a racing mind state, the mask changes the type of auditory output. In an example, the virtual sleep coach stops narrating a story and begins a guided imagery exercise where the coach attempts to evoke mental images. In another example, the sleep coach continues the narrative, and the relaxation mask outputs lights modulated to correlate to the narrative. In yet another example, the sleep coach continues the narrative and a gentle haptic output is output by a tactile motor, in an effort to regain the subject's attention.

Despite the adjusted output, in aspects, the biometric parameters indicate the subject's attention is still wandering. In response, the relaxation mask further adjusts an output. In an example, the mask may adjust the speed of modulated lights, change the type of auditory output by starting a guided meditation, guided imagery exercise, or outputting music.

In aspects, the mask collects historical information regarding which output stimulus or combination of output stimuli regained the subject's attention and which output stimulus, or combination of output stimuli did not regain the subject's attention. Through a machine learning algorithm, this historical information is used to create a smart, adaptive system that intelligently selects how to adjust an output stimulus for a specific subject in response to a racing mind state.

In one example, the relaxation mask includes at least one EEG sensor configured to collect a signal from the subject's frontal or prefrontal cortex region. In an aspect, the relaxation mask outputs a sensory stimulus that is one of auditory, haptic, or visual. The relaxation mask receives output data from the EEG sensor. The relaxation mask correlates the output data with the sensory stimulus to identify when a subject has a racing mind. In response to an identified racing mind, an AI program adjusts an output of the relaxation mask and the relaxation mask outputs the adjusted output.

In an example, a relaxation mask includes a first electrode configured to detect an EEG signal from the frontal cortex of prefrontal cortex of a subject, a second electrode configured to detect at least one of an EOG signal, ECG signal, GSR, or PPG signal from the forehead region of the subject, in-ear earpieces configured to output audio signals, a light pipe disposed around eye cavities of the relaxation mask, and a tactile motor disposed over the temporal lobe of the subject. The relaxation mask is configured to output an auditory sensory stimulus and correlate the EEG signal, the information obtained using the second electrode, and the sensory stimulus to determine if the subject is in a racing mind state. If so, the mask adjusts at least one stimulus based on the determined racing mind state and outputs the adjusted stimulus.

In an aspect, a microphone on the mask or on a paired device in communication with the mask detects noise in the subject's environment. One or more of the mask, a paired device, or a network determines whether there is a correlation between noise detected by the microphone and measurements from information collected using one or more of the sensors. In an example, the microphone detects noise in the subject's vicinity correlates with an increase in the subjects EEG signal. In response, the mask takes action in an effort to lower the subject's EEG and help the subject relax. In one example, the mask outputs a masking sound, amplifies a masking sound, or alters the spectral output of a masking sound.

In an example, if at 606, the subject is determined to be focused on the sensory output and therefore not have a racing mind, the relaxation mask continues to output the stimulus or a version of the stimulus until a subject is determined to be asleep. In aspects, the mask gradually decreases the sound pressure level of an audio output, slowly decreases the intensity of lights, and decreases haptic outputs when biometric information indicates the subject is asleep. After the subject is determined to be asleep for a predetermined, configurable amount of time, the mask stops outputting, at least, certain stimuli.

The smart relaxation mask uses biometric information from a subject to determine the subject has a racing mind. In response to the determination, the mask adjusts one or more outputs in an effort to shift the subject's focus to the output of the mask and guide the subject to a state of relaxation. This helps the subject relax and fall asleep. The relaxation helps increase a subject's wellness by helping them more consistently fall and stay asleep. The relaxation mask helps treat diagnosable medical conditions, such as insomnia.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the Figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. A relaxation mask comprising:
a mask having a pair of eye cavities comprising a first eye cavity and a second eye cavity, each of the first eye cavity and the second eye cavity of the pair of eye cavities configured to cover a closed eyelid of a subject wearing the relaxation mask;
a first strap, extending from the first eye cavity, configured to have a low profile around a first temple of the subject;
a second strap, extending from the second eye cavity, configured to have a low profile around a second temple of the subject, wherein the first strap and the second strap are configured to adjustably fit around, at least, a portion of a head of the subject;
a first in-ear earpiece extending from the first strap;
a second in-ear earpiece extending from the second strap;
at least one biometric sensor configured to output data associated with the subject, wherein the at least one biometric sensor comprises a first electrode configured to contact Fp1 on a prefrontal cortex of the subject and a second electrode configured to contact Fp2 on the prefrontal cortex, wherein the first electrode and the second electrode are disposed above the pair of eye cavities;
a light pipe disposed around the pair of eye cavities;
a removable liner covering the pair of eye cavities and the light pipe;
a memory coupled to a processor; and
instructions stored in the memory that, when executed, cause the processor to:
output, via at least one stimulator, a sensory stimulus;
receive the output data from the at least one biometric sensor;
correlate the output data and the sensory stimulus to identify a racing mind state;
adjust one or more of an auditory, haptic, or visual stimulus of the relaxation mask in response to the identified racing mind state; and
output, via the at least one stimulator, the adjusted one or more auditory, haptic, or visual stimulus.

2. The relaxation mask of claim 1, wherein at least one of the first electrode and the second electrode is configured to collect an electroencephalogram (EEG) signal of the subject.

3. The relaxation mask of claim 1, wherein at least one of the first electrode and the second electrode collects is configured to collect an electroencephalogram (EEG) signal from at least one of a frontal cortex or the prefrontal cortex of the subject and at least one of: an electrooculography (EOG) signal, electrocardiogram (ECG) signal, galvanic skin response (GSR), or photoplethysmogram (PPG) signal from a forehead of the subject.

4. The relaxation mask of claim 1, wherein the sensory stimulus comprises:
one of a guided mediation track or soundscape.

5. The relaxation mask of claim 1, wherein:
the output data comprises an electroencephalogram (EEG) signal; and
the correlating comprises determining low activity in the EEG signal when the sensory stimulus, occupying a particular range of frequencies, is output.

6. The relaxation mask of claim 1, wherein the instructions further cause the processor to:
continue to receive the output data from the at least one biometric sensor after outputting the adjusted one or more auditory, haptic, or visual stimulus;
continuously correlate the received output data and the adjusted one or more auditory, haptic, or visual stimulus to determine if the subject continues to have the racing mind state; and
in response to determining the continued racing mind state, further adjusting and outputting the at least one auditory, haptic, or visual stimulus.

7. The relaxation mask of claim 1, wherein the instructions cause the processor to adjust one or more of the auditory, haptic, or visual stimulus of the relaxation mask by:
introducing, via the light pipe, visual cues which modulate to coincide with the sensory stimulus.

8. The relaxation mask of claim 1, wherein the processor is configured to adjust one or more of the auditory, haptic, or visual stimulus of the relaxation mask by:
introducing, via a tactical motor, a haptic output in an effort to guide the subject to focus on the sensory stimulus.

9. The relaxation mask of claim 1, wherein the processor is configured to adjust one or more of the auditory, haptic, or visual stimulus of the relaxation mask by:
changing a simulated environment using any combination of auditory, haptic, or visual cues.

10. The relaxation mask of claim 1, wherein the first in-ear earpiece and the second in-ear earpiece each have a conductive ear tip configured to contact locations between a temporal and parietal lobe of the subject, wherein the output data includes information collected by each in-ear earpiece.

11. The relaxation mask of claim 10, wherein the ear tip of the first in-ear earpiece is configured to contact TP9 and the ear tip of the second in-ear earpiece is configured to contact TP10.

12. A relaxation mask comprising:
a mask having a pair of eye cavities comprising a first eye cavity and a second eye cavity, each of the first eye cavity and the second eye cavity of the pair of eye cavities configured to cover a closed eyelid of a subject wearing the relaxation mask;
a first strap, extending from the first eye cavity, configured to have a low profile around a first temple of the subject;
a second strap, extending from the second eye cavity, configured to have a low profile around a second temple of the subject, wherein the first strap and the second strap are configured to adjustably fit around, at least, a portion of a head of the subject;
a first conductive in-ear earpiece extending from the first strap and configured to obtain a first set of biometric information and output a first set of audio signals;
a second conductive in-ear earpiece extending from the second strap and configured to obtain a second set of biometric information and output a second set of audio signals;
at least one biometric sensor providing output data, wherein the least one biometric sensor comprises a first electrode configured to contact Fp1 on a prefrontal cortex of the subject wearing the mask and a second electrode configured to contact Fp2 on the prefrontal cortex, wherein the first electrode and the second electrode are disposed above the pair of eye cavities;
a light pipe disposed around the pair of eye cavities;
a removable liner covering the pair of eye cavities and the light pipe:
a memory coupled to a processor; and
instructions stored in the memory that, when executed, cause the processor to:
output, at least one sensory stimulus;
receive the output data from the at least one biometric sensor;
correlate the output data and the at least one sensory stimulus to identify a racing mind state;
execute an artificial intelligence (AI) program that adjusts the at least one sensory stimulus of the relaxation mask in response to the identified racing mind state; and
output the adjusted at least one sensory stimulus.

13. The relaxation mask of claim 12, wherein the first conductive in-ear earpiece comprises a first eartip configured to contact TP9 and the second conductive in-ear earpiece comprises a second eartip configured to contact TP10.

14. The relaxation mask of claim 12, wherein the instructions further cause the processor to provide an active noise reduction signal to the first and second in-ear earpieces.

15. The relaxation mask of claim 12, wherein the AI program is configured to adjust one or more of an auditory, haptic, or visual output to guide the subject to focus on the at least one sensory stimulus.

16. The relaxation mask of claim 12, wherein the instructions are configured to cause the processor to:
  continuously correlate the received output data and an adjusted output signal to determine the subject remains in the racing mind state;
  further adjust the at least one sensory stimulus based on the subject remaining in the racing mind state; and
  output the further adjusted at least one sensory stimulus.

17. The relaxation mask of claim 16, wherein:
  the adjusted output signal comprises spoken words and the further adjusted at least one sensory stimulus comprises lights output via the light pipe, wherein the lights are modulated to correlate to the spoken words.

18. The relaxation mask of claim 16, further comprising:
  a tactile motor, wherein
  the at least one further adjusted at least one sensory stimulus comprises a haptic output from the tactile motor.

19. The relaxation mask of claim 12, further comprising:
  a transceiver, wherein the transceiver is configured to communicate with an external wireless device to receive the sensory stimulus to be output by the relaxation mask.

20. A relaxation mask comprising:
  a mask having a pair of eye cavities comprising a first eye cavity and a second eye cavity, each of the first eye cavity and the second eye cavity of the pair of eye cavities configured to cover a closed eyelid of a subject wearing the relaxation mask;
  a first strap, extending from the first eye cavity, configured to have a low profile around a first temple of the subject;
  a second strap, extending from the second eye cavity, configured to have a low profile around a second temple of the subject, wherein the first strap and the second strap are configured to adjustably fit around, at least, a portion of a head of the subject;
  a first conductive in-ear earpiece extending from the first strap and configured to obtain a first set of biometric information and output a first set of audio signals;
  a second conductive in-ear earpiece extending from the second strap and configured to obtain a second set of biometric information and output a second set of audio signals;
  at least one biometric sensor, wherein the at least one biometric sensor comprises a first electrode configured to contact Fp1 on a prefrontal cortex of the subject wearing the mask and a second electrode configured to contact Fp2 on the prefrontal cortex;
  a light pipe disposed around the pair of eye cavities;
  a removable liner covering the pair of eye cavities and the light pipe:
  a tactile motor configured to be disposed over a temporal lobe of the subject;
  a processor;
  a memory coupled to the processor; and
  instructions stored in the memory that, when executed, cause the processor to:
    output, at least one sensory stimulus;
    receive output data from the at least one biometric sensor;
    determine, based on a correlation of the output data and the at least one sensory stimulus, the subject is in a racing mind state;
    adjust the at least one sensory stimulus of the relaxation mask based on the determined racing mind state, wherein adjusting the at least one output of the relaxation mask comprises one or more of:
      adjusting an auditory sensory stimulus, introducing at least one visual cue via the light pipe, or introducing at least one haptic cue via the tactile motor, and
    output the at least one adjusted sensory stimulus.

21. The relaxation mask of claim 20, wherein the processor is configured to:
  continuously monitor the output data;
  correlate both the continuously monitored output data with the at least one adjusted sensory stimulus to determine the subject remains in the racing mind state; and
  in response to the determining the subject remains in the racing mind state, further adjust the at least one adjusted output sensory stimulus.

* * * * *